(12) United States Patent
Jonkman

(10) Patent No.: US 11,524,138 B2
(45) Date of Patent: Dec. 13, 2022

(54) CATHETERS FOR EXTRACORPOREAL CIRCULATION

(71) Applicant: Michigan Critical Care Consultants, Inc., Dexter, MI (US)

(72) Inventor: Kenneth Jonkman, South Lyon, MI (US)

(73) Assignee: Michigan Critical Care Consultants, Inc., Dexter, MI (US)

( * ) Notice: Subject to any disclaimer, the term of this patent is extended or adjusted under 35 U.S.C. 154(b) by 444 days.

(21) Appl. No.: 16/615,034

(22) PCT Filed: Jun. 27, 2018

(86) PCT No.: PCT/US2018/039661
§ 371 (c)(1),
(2) Date: Nov. 19, 2019

(87) PCT Pub. No.: WO2019/005903
PCT Pub. Date: Jan. 3, 2019

(65) Prior Publication Data
US 2020/0171274 A1    Jun. 4, 2020

Related U.S. Application Data

(60) Provisional application No. 62/525,280, filed on Jun. 27, 2017.

(51) Int. Cl.
*A61M 25/00* (2006.01)
*A61M 25/01* (2006.01)
(52) U.S. Cl.
CPC ...... *A61M 25/003* (2013.01); *A61M 25/0105* (2013.01); *A61M 2025/0031* (2013.01)

(58) Field of Classification Search
CPC .. A61M 2025/0031; A61M 2025/0037; A61M 25/007; A61M 25/0071
See application file for complete search history.

(56) References Cited

U.S. PATENT DOCUMENTS 4,129,129 A * 12/1978 Amrine ............... A61M 1/3659
600/16
4,406,656 A    9/1983 Hattler
(Continued)

FOREIGN PATENT DOCUMENTS

| CN | 202637572 U | 1/2013 |
| CN | 210409089 U | 4/2020 |
| EP | 0386408 A1  | 9/1990 |

OTHER PUBLICATIONS

International Searching Authority. International Search Report and Written Opinion for PCT application No. PCT/US2018/039661, dated Sep. 21, 2018, pp. 1-14.
(Continued)

*Primary Examiner* — Nathan R Price
*Assistant Examiner* — Courtney B Fredrickson
(74) *Attorney, Agent, or Firm* — Price Heneveld LLP

(57) ABSTRACT

Catheter and catheter assemblies for extracorporeal circulation of body fluids, such as blood, are described. A catheter includes a septum that divides an internal lumen into fluidicly isolated drainage and infusion lumens. The infusion lumen extends along only a portion of the axial length of the catheter and terminates at an infusion opening defined by the circumferential wall of the elongate member of the catheter. The drainage lumen extends the full axial length of the catheter and is laterally accessible via first and second sets of drainage openings.

18 Claims, 13 Drawing Sheets

(56) References Cited

U.S. PATENT DOCUMENTS

| | | |
|---|---|---|
| 4,451,252 A | 5/1984 | Martin |
| 4,738,666 A | 4/1988 | Fuqua |
| 5,009,636 A | 4/1991 | Wortley et al. |
| 5,190,528 A | 3/1993 | Fonger et al. |
| 5,405,320 A | 4/1995 | Twardowski et al. |
| 5,413,557 A | 5/1995 | Solar |
| 5,421,825 A | 6/1995 | Farcot |
| 5,464,398 A | 11/1995 | Haindl |
| 5,618,267 A | 4/1997 | Palestrant |
| 5,858,009 A | 1/1999 | Jonkman |
| 5,868,717 A | 2/1999 | Prosl et al. |
| 5,916,193 A | 6/1999 | Stevens et al. |
| 6,238,409 B1 | 5/2001 | Hojeibane |
| 6,285,903 B1 | 9/2001 | Rosenthal et al. |
| 7,473,237 B2 | 1/2009 | Wang et al. |
| 3,002,729 A1 | 8/2011 | Melsheimer et al. |
| 2005/0004504 A1 | 1/2005 | Frye et al. |
| 2005/0085761 A1* | 4/2005 | Wang ............... A61M 1/3653 604/4.01 |
| 2008/0103480 A1 | 5/2008 | Bosel et al. |
| 2011/0009935 A1 | 1/2011 | Kane et al. |
| 2011/0144620 A1* | 6/2011 | Tal ............... A61M 25/0108 604/529 |
| 2012/0232470 A1 | 9/2012 | Hardert et al. |
| 2014/0330220 A1 | 11/2014 | Zawacki et al. |
| 2016/0303354 A1* | 10/2016 | Burkett ............... A61B 5/14552 |
| 2017/0035987 A1 | 2/2017 | Ardehali |

OTHER PUBLICATIONS

The International Bureau of WIPO. International Preliminary Report on Patentability for PCT application No. PCT/US2018/039661, dated Dec. 31, 2019, pp. 1-7.

Okamoto, T. et al., "Preliminary Experiment with a Newly Developed Double Balloon, Double Lumen Catheter for Extracorporeal Life Support Vascular Access." ASAIO Journal, Sep.-Oct. 2003, pp. 583-588, vol. 49, Issue 5.

Ichiba, S. et al., "Modifying a Venovenous Extracorporeal Membrane Oxygenation Circuit to Reduce Recirculation," The Society for Thoracic Surgeons, 2000, pp. 298-299, Elsevier Science Inc.

Otsu, T. et al., "Laboratory Evaluation of a Double Lumen Catheter for Venovenous Neonatal ECMO." Trans Am Soc Artif Intern Organs. Jul.-Sep. 1989, pp. 647-650, vol. XXXV, American Society of Artifical Internal Organs.

Delius. R. et al. "Venovenous compares favorably with venoarterial access for extracorporeal membrane oxygenation in neonatal respiratory failure." The Jouranl of Thoracic and Cardiovascular Surgery. Aug. 1993, pp. 329-338, vol. 106, Issue 2.

* cited by examiner

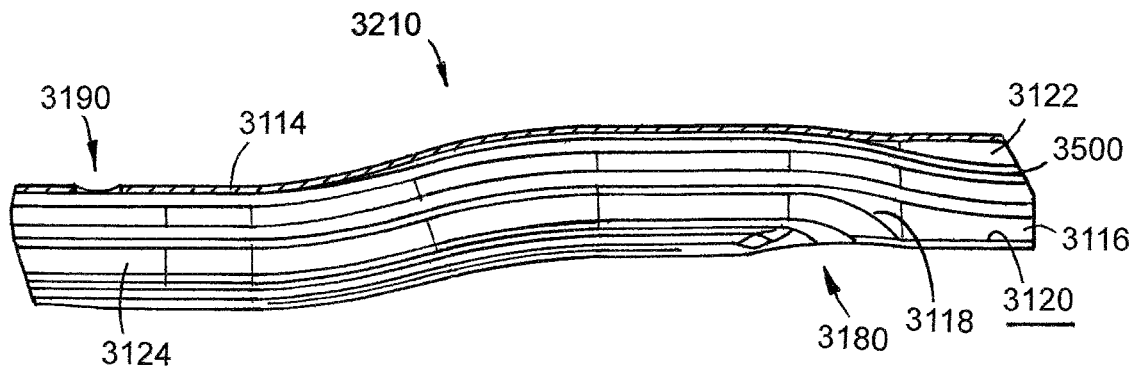
FIG.9B
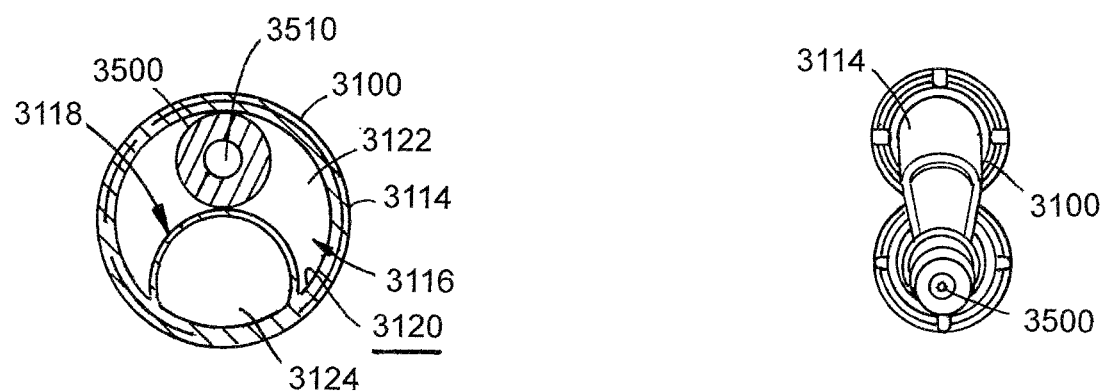
FIG.9C
FIG.9D

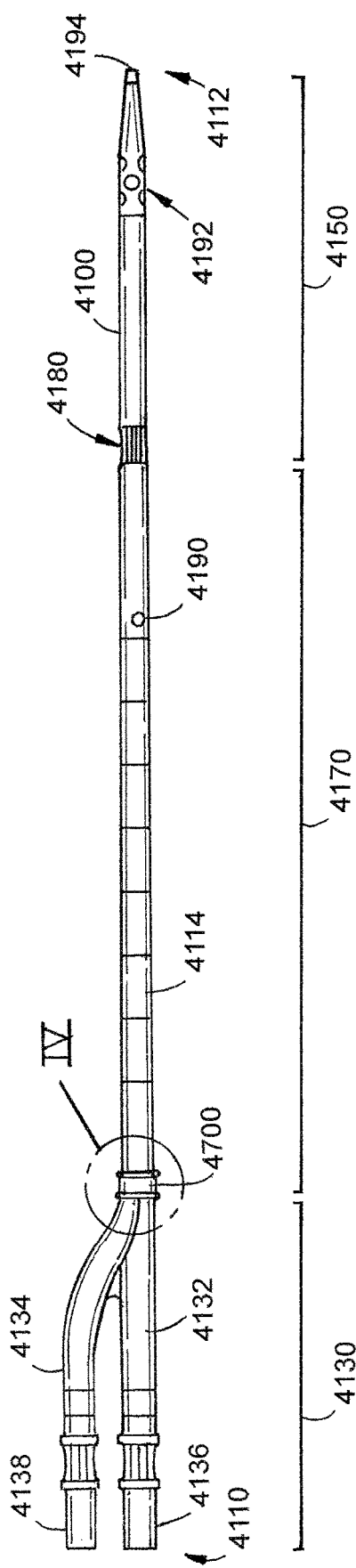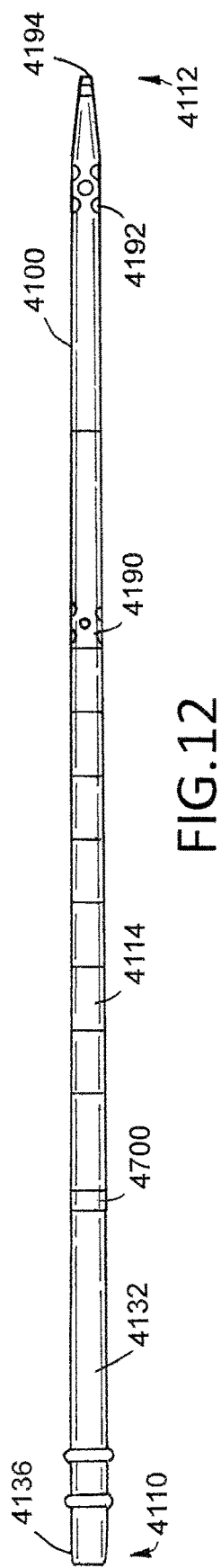
FIG.11
FIG.12

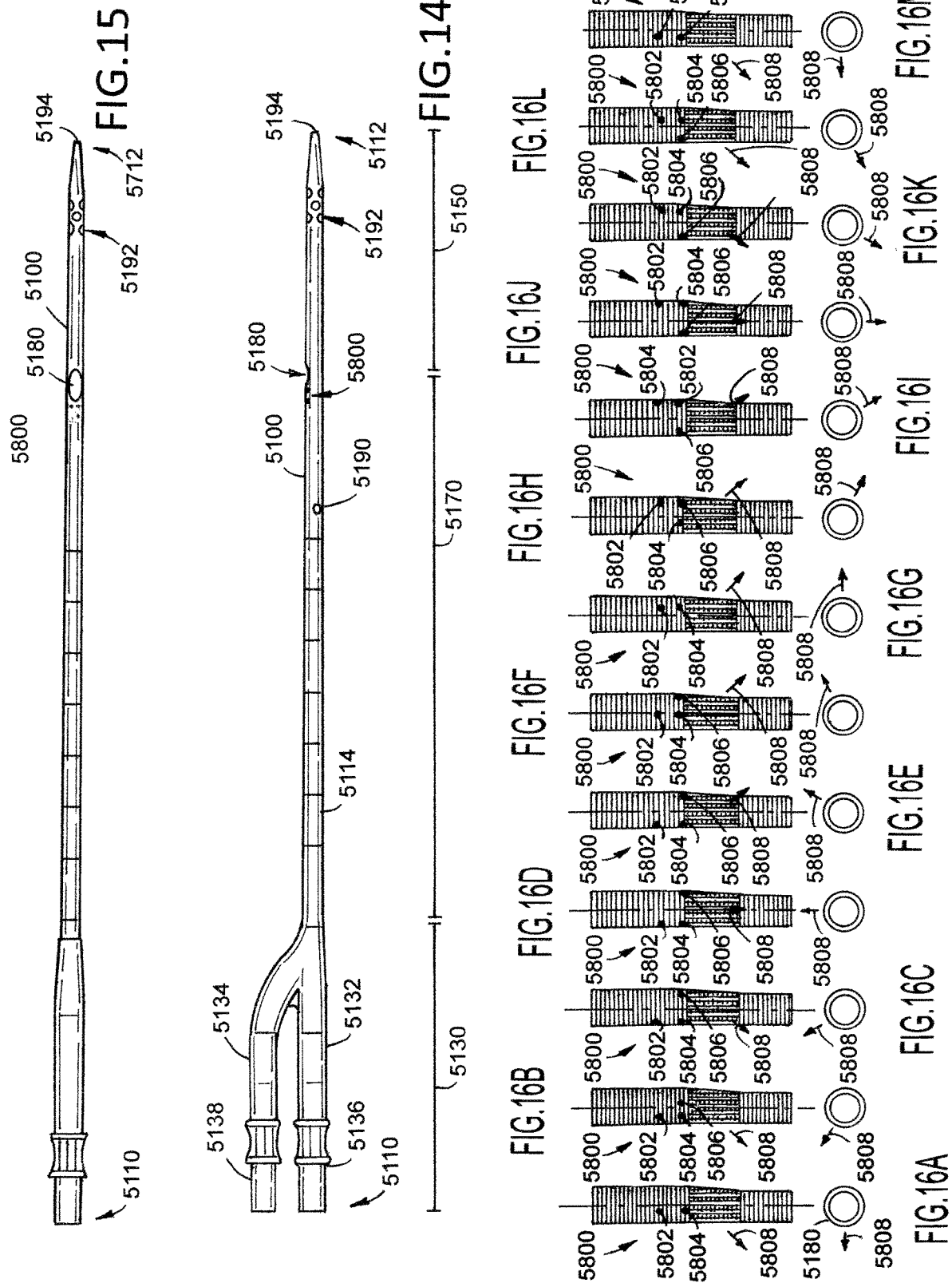

CATHETERS FOR EXTRACORPOREAL CIRCULATION

FIELD

The disclosure relates to the field of medical devices. More particularly, the disclosure relates to catheters and catheter assemblies useful in the extracorporeal circulation of body fluids. Specific examples described in the disclosure relate to catheters useful for extracorporeal oxygenation of blood.

BACKGROUND

Extracorporeal circuits are used in a variety of medical treatments. For example, extracorporeal membrane oxygenation (ECMO) uses an extracorporeal circuit to oxygenate the blood of a patient whose heart and lungs, for a variety of reasons, are unable to achieve sufficient natural gas exchange. During ECMO, deoxygenated blood is routed outside the body to an extracorporeal circuit within which artificial gas exchange is performed. Following oxygenation, the blood is infused back into the natural circulation of the body.

Catheters are a critical component of all extracorporeal circuits as they provide the points at which body fluid(s) enter and exit the circuit. In ECMO, for example, a catheter is placed within the vena cava of the patient. Venous blood enters the catheter and moves into the extracorporeal circuit. Following oxygenation, blood circulates back to the same or a different catheter and, ultimately, returns to the body as oxygenated blood.

The art describes a variety of catheters suitable for use in a variety of extracorporeal circuits. For example, the art describes several double lumen catheters, which provide both a drainage and a return lumen, as suitable for use in ECMO. These catheters have been well-received and are considered advantageous for several reasons, including the need for only a single cannulation. The inclusion of drainage and return functions in the same device, however, presents several challenges.

A need exists, therefore, for improved catheters for extracorporeal circulation of body fluids, including catheters for extracorporeal blood oxygenation.

BRIEF SUMMARY OF SELECTED EXAMPLES

Various example catheters and catheter assemblies are described.

An example catheter comprises an elongate member having a proximal end defining an infusion port and a drainage port, a distal end defining a distal opening, a proximal portion extending from the proximal end toward the distal end, a distal portion extending from the distal end toward the proximal end, a main body extending between the proximal and distal portions, and a circumferential wall extending between the proximal and distal ends. The main body has a first outer diameter that is substantially uniform along the axial length of the main body. The distal portion includes a distal extension, a distal tip, a first tapered portion, and a second tapered portion. The distal extension has a second outer diameter that is less than the first outer diameter and the distal tip has a third outer diameter that is less than the second outer diameter. The first tapered portion is disposed between the main body and the distal extension and the second tapered portion is disposed between the distal extension and the distal tip. The circumferential wall has an internal surface defining an internal lumen, and defines an infusion opening, and first and second sets of drainage openings. The infusion opening and each drainage opening of the first and second sets of drainage openings is a passageway through the thickness of the circumferential wall. A septum is disposed on and is continuous with the internal surface of the circumferential wall. The septum divides the internal lumen into fluidicly isolated drainage and infusion lumens. The drainage lumen extends between the drainage port and the distal opening, with each opening of the first and second sets of drainage openings providing fluid access to the drainage lumen. The infusion lumen extends between the infusion port and the infusion opening.

Another example catheter comprises an elongate member having a proximal end defining an infusion port and a drainage port, a distal end defining a distal opening, a proximal portion extending from the proximal end toward the distal end, a distal portion extending from the distal end toward the proximal end, a main body extending between the proximal and distal portions, and a circumferential wall extending between the proximal and distal ends. The main body has a first outer diameter that is substantially uniform along the axial length of the main body. The distal portion includes a distal extension, a distal tip, a first tapered portion, and a second tapered portion. The distal extension has a second outer diameter that is less than the first outer diameter and the distal tip has a third outer diameter that is less than the second outer diameter. The first tapered portion is disposed between the main body and the distal extension and the second tapered portion is disposed between the distal extension and the distal tip. The circumferential wall has an internal surface defining an internal lumen, and defines an infusion opening, and first and second sets of drainage openings. The infusion opening and each drainage opening of the first and second sets of drainage openings is a passageway through the thickness of the circumferential wall. A septum is disposed on and is continuous with the internal surface of the circumferential wall. The septum divides the internal lumen into fluidicly isolated drainage and infusion lumens. The drainage lumen extends between the drainage port and the distal opening, with each opening of the first and second sets of drainage openings providing fluid access to the drainage lumen. The infusion lumen extends between the infusion port and the infusion opening. The first set of drainage openings is disposed proximal to the infusion opening and the second set of drainage openings is disposed distal to the infusion opening.

Another example catheter comprises an elongate member having a proximal end defining an infusion port and a drainage port, a distal end defining a distal opening, a proximal portion extending from the proximal end toward the distal end, a distal portion extending from the distal end toward the proximal end, a main body extending between the proximal and distal portions, and a circumferential wall extending between the proximal and distal ends. The main body has a first outer diameter that is substantially uniform along the axial length of the main body. The distal portion includes a distal extension, a distal tip, a first tapered portion, and a second tapered portion. The distal extension has a second outer diameter that is less than the first outer diameter and the distal tip has a third outer diameter that is less than the second outer diameter. The first tapered portion is disposed between the main body and the distal extension and the second tapered portion is disposed between the distal extension and the distal tip. The circumferential wall has an internal surface defining an internal lumen, and defines an infusion opening, and first and second sets of drainage openings. The infusion opening and each drainage opening of the first and second sets of drainage openings is a passageway through the thickness of the circumferential wall. A septum is disposed on and is continuous with the internal surface of the circumferential wall. The septum divides the internal lumen into fluidicly isolated drainage and infusion lumens. The drainage lumen extends between the drainage port and the distal opening, with each opening of the first and second sets of drainage openings providing fluid access to the drainage lumen. The infusion lumen extends between the infusion port and the infusion opening. The infusion opening is disposed axially between the first and second sets of drainage openings.

Another example catheter comprises an elongate member having a proximal end defining an infusion port and a drainage port, a distal end defining a distal opening, a proximal portion extending from the proximal end toward the distal end, a distal portion extending from the distal end toward the proximal end, a main body extending between the proximal and distal portions, and a circumferential wall extending between the proximal and distal ends. The main body has a first outer diameter that is substantially uniform along the axial length of the main body. The distal portion includes a distal extension, a distal tip, a first tapered portion, and a second tapered portion. The distal extension has a second outer diameter that is less than the first outer diameter and the distal tip has a third outer diameter that is less than the second outer diameter. The first tapered portion is disposed between the main body and the distal extension and the second tapered portion is disposed between the distal extension and the distal tip. The circumferential wall has an internal surface defining an internal lumen, and defines an infusion opening, and first and second sets of drainage openings. The infusion opening and each drainage opening of the first and second sets of drainage openings is a passageway through the thickness of the circumferential wall. A septum is disposed on and is continuous with the internal surface of the circumferential wall. The septum divides the internal lumen into fluidicly isolated drainage and infusion lumens. The drainage lumen extends between the drainage port and the distal opening, with each opening of the first and second sets of drainage openings providing fluid access to the drainage lumen. The infusion lumen extends between the infusion port and the infusion opening. The first set of drainage openings is disposed proximal to the infusion opening and extends along only a portion of the circumference of the main body of the catheter. The second set of drainage openings is disposed distal to the infusion opening and extends along the entire circumference of the distal portion of the catheter.

Another example catheter comprises an elongate member having a proximal end defining an infusion port and a drainage port, a distal end defining a distal opening, a proximal portion extending from the proximal end toward the distal end, a distal portion extending from the distal end toward the proximal end along a first longitudinal axis, a main body extending between the proximal and distal portions along a second longitudinal axis substantially parallel to the first longitudinal axis, an offset portion extending between the main body and distal portions, and a circumferential wall extending between the proximal and distal ends. The main body has a first outer diameter that is substantially uniform along the axial length of the main body. The circumferential wall has an internal surface defining an internal lumen, and defines an infusion opening, a first set of drainage openings on the main body, and a second set of drainage openings on the distal portion. The infusion opening and each drainage opening of the first and second sets of drainage openings is a passageway through the thickness of the circumferential wall. A septum is disposed on and is continuous with the internal surface of the circumferential wall. The septum divides the internal lumen into fluidicly isolated drainage and infusion lumens. The drainage lumen extends between the drainage port and the distal opening, with each opening of the first and second sets of drainage openings providing fluid access to the drainage lumen. The infusion lumen extends between the infusion port and the infusion opening.

Another example catheter comprises an elongate member having a proximal end defining an infusion port and a drainage port, a distal end defining a distal opening, a proximal portion extending from the proximal end toward the distal end, a distal portion extending from the distal end toward the proximal end along a first longitudinal axis, a main body extending between the proximal and distal portions along a second longitudinal axis substantially parallel to the first longitudinal axis, an offset portion extending between the main body and distal portions, and a circumferential wall extending between the proximal and distal ends. The main body has a first outer diameter that is substantially uniform along the axial length of the main body. The circumferential wall has an internal surface defining an internal lumen, and defines an infusion opening, a first set of drainage openings on the main body, and a second set of drainage openings on the distal portion. The infusion opening and each drainage opening of the first and second sets of drainage openings is a passageway through the thickness of the circumferential wall. A septum is disposed on and is continuous with the internal surface of the circumferential wall. The septum divides the internal lumen into fluidicly isolated drainage and infusion lumens. The drainage lumen extends between the drainage port and the distal opening, with each opening of the first and second sets of drainage openings providing fluid access to the drainage lumen. The infusion lumen extends between the infusion port and the infusion opening. The infusion opening is disposed axially distal to the first and second sets of drainage openings.

Another example catheter comprises an elongate member having a proximal end defining an infusion port and a drainage port, a distal end defining a distal opening, a proximal portion extending from the proximal end toward the distal end, a distal portion extending from the distal end toward the proximal end along a first longitudinal axis, a main body extending between the proximal and distal portions along a second longitudinal axis substantially parallel to the first longitudinal axis, an offset portion extending between the main body and distal portions, and a circumferential wall extending between the proximal and distal ends. The main body has a first outer diameter that is substantially uniform along the axial length of the main body. The circumferential wall has an internal surface defining an internal lumen, and defines an infusion opening, a first set of drainage openings on the main body, and a second set of drainage openings on the distal portion. The infusion opening and each drainage opening of the first and second sets of drainage openings is a passageway through the thickness of the circumferential wall. A septum is disposed on and is continuous with the internal surface of the circumferential wall. The septum divides the internal lumen into fluidicly isolated drainage and infusion lumens. The drainage lumen extends between the drainage port and the distal opening, with each opening of the first and second sets of drainage openings providing fluid access to the drainage lumen. The infusion lumen extends between the infusion port and the infusion opening. The infusion opening is disposed axially between the first and second sets of drainage openings.

Additional understanding of the claimed medical devices can be obtained by reviewing the detailed description of selected examples, below, with reference to the appended drawings.

DESCRIPTION OF FIGURES

FIG. 9B is an enlarged sectional view of area III in FIG. 9A.

FIG. 9C is an enlarged sectional view of the third example catheter assembly, taken along line 9C-9C in FIG. 6A.

FIG. 9D is an distal end view of the third example catheter assembly.

FIG. 11 is a perspective view of an example catheter.

FIG. 12 is a bottom view of the example catheter illustrated in FIG. 11.

FIG. 14 is a perspective view of another example catheter.

FIG. 15 is a top view of the example catheter illustrated in FIG. 14.

FIG. 16A is a top view of a portion of the example catheter illustrated in FIG. 14. The catheter is positioned in a first circumferential orientation.

FIG. 16B is a top view of a portion of the example catheter illustrated in FIG. 14. The catheter is positioned in another circumferential orientation.

FIG. 16C is a top view of a portion of the example catheter illustrated in FIG. 14. The catheter is positioned in another circumferential orientation.

FIG. 16D is top view of a portion of the example catheter illustrated in FIG. 14. The catheter is positioned in another circumferential orientation.

FIG. 16E is a top view of a portion of the example catheter illustrated in FIG. 14. The catheter is positioned in another circumferential orientation.

FIG. 16F is a top view of a portion of the example catheter illustrated in FIG. 14. The catheter is positioned in another circumferential orientation.

FIG. 16G is a top view of a portion of the example catheter illustrated in FIG. 14. The catheter is positioned in another circumferential orientation.

FIG. 16H is a top view of a portion of the example catheter illustrated in FIG. 14. The catheter is positioned in another circumferential orientation.

FIG. 16I is a top view of a portion of the example catheter illustrated in FIG. 14. The catheter is positioned in another circumferential orientation.

FIG. 16J is a top view of a portion of the example catheter illustrated in FIG. 14. The catheter is positioned in another circumferential orientation.

FIG. 16K is top view of a portion of the example catheter illustrated in FIG. 14. The catheter is positioned in another circumferential orientation.

FIG. 16L is a top view of a portion of the example catheter illustrated in FIG. 14. The catheter is positioned in another circumferential orientation.

FIG. 16M is a top view of a portion of the example catheter illustrated in FIG. 14. The catheter is positioned in another circumferential orientation.

DETAILED DESCRIPTION OF SELECTED EXAMPLES

The following detailed description and the appended drawings describe and illustrate various example catheters and catheter assemblies. The description and illustration of these examples are provided to enable one skilled in the art to make and use the inventive catheters and catheter assemblies. They are not intended to limit the scope of the claims in any manner.

As used herein, the term "catheter" refers to an elongate tubular medical device that defines at least one lumen.

As used herein, the term "catheter assembly" refers to an elongate tubular medical device that defines at least one lumen and that has an elongate component, such as an introducer, slidably disposed within the at least one lumen.

FIGS. 1, 2, 3, 4, 4A, 4B, 4C, and 4D illustrate a first example catheter assembly 1000. The catheter assembly 1000 includes catheter 1100 and introducer 1500.

Catheter 1100 is an elongate member that extends from a proximal end 1110 to a distal end 1112 along a longitudinal axis (not illustrated in the Figures). A circumferential wall 1114 extends between the proximal 1110 and distal 1112 ends and defines an internal lumen 1116. A septum 1118 extends inwardly from the internal surface 1120 of the circumferential wall 1114 and divides the internal lumen 1114 into a drainage 1122 lumen and an infusion lumen 1124. Within the catheter 1100 and independent of its connection to a fluid circuit, septum 1118 physically separates drainage lumen 1122 from infusion lumen 1124 such that the drainage 1122 and infusion 1124 lumens are not in fluid communication with each other.

Figure 3:
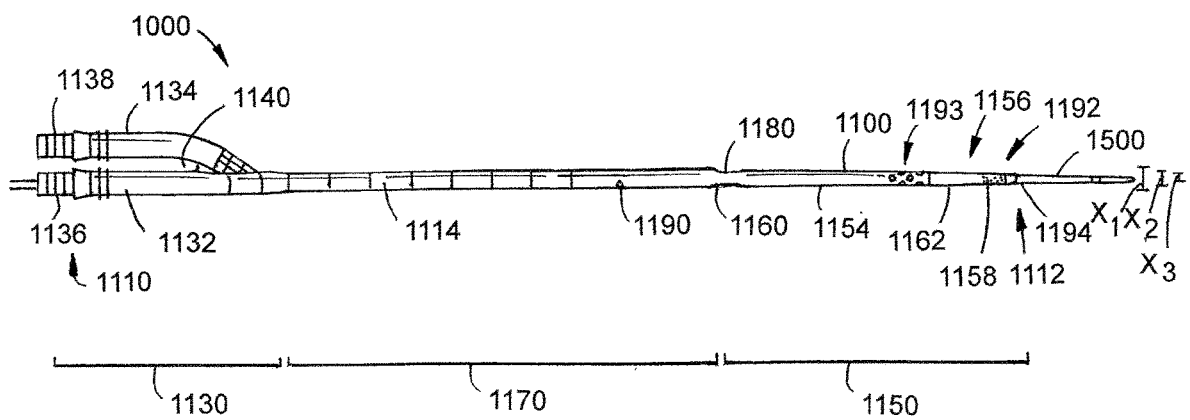
FIG. 3 is a side view of the first example catheter assembly.

As best illustrated in FIG. 3, a proximal portion 1130 extends distally from the proximal end 1110 and toward the distal end 1112. A distal portion 1150 extends proximally from the distal end 1112 and toward the proximal end 1110. A main body 1170 is disposed between the proximal 1130 and distal 1150 portions.

The proximal portion 1130 includes drainage port 1132 and infusion port 1134. The drainage port 1132 is in fluid communication with the drainage lumen 1122 while infusion port 1134 is in fluid communication with the infusion lumen 1124. A first connector 1136 is disposed on the drainage port 1132 and a second connector 1138 is disposed on the infusion port 1134. Each of the connectors 1136, 1138 defines suitable structure for connecting the respective port 1132, 1134 to an element of a fluid circuit, such as tubing in an extracorporeal circuit. In the illustrated embodiment, the connectors 1136, 1138 comprise separate members that are attached to the respective port 1132, 1134. Integrally-formed connectors could be used as an alternative, if desired.

The drainage 1132 and infusion 1134 ports are fluidicly separated from each other. In the illustrated embodiment, the ports 1132, 1134 are physically separated from each other by a bifurcation 1140 in the circumferential wall 1114 of the catheter 1100. Inclusion of the bifurcation 1140 is considered advantageous at least because it maintains the fluidic separation of the drainage 1132 and infusion ports 1134 while also facilitating establishment of connections to the ports 1132, 1134, it is considered optional.

Figure 4:
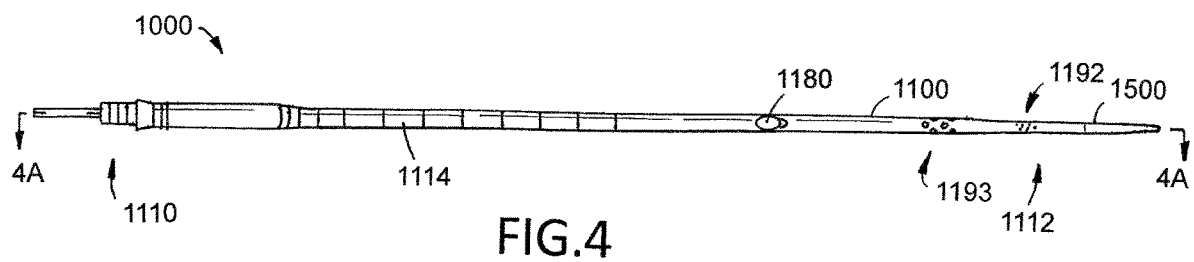
FIG. 4 is a top view of the first example catheter assembly.
Figure 4A:
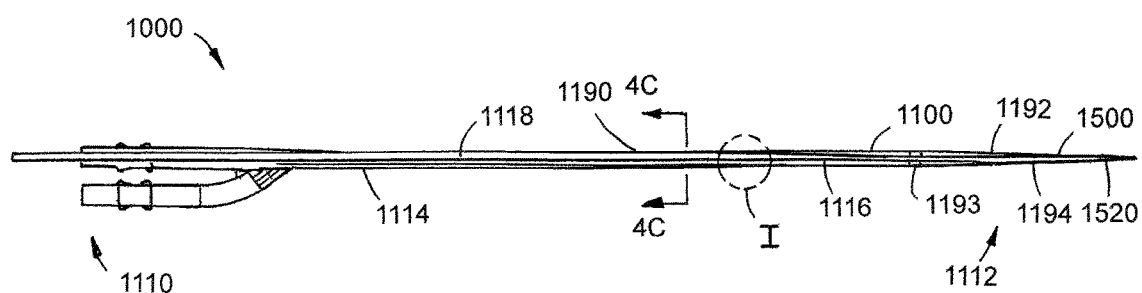
FIG. 4A is a sectional view of the first example catheter assembly, taken along line 4A-4A in FIG. 4.
Figure 4B:
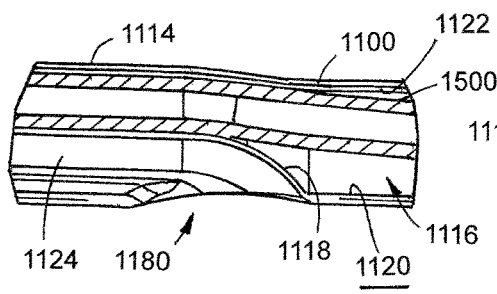
FIG. 4B is an enlarged sectional view of area I in FIG. 4A.
Figure 4C:
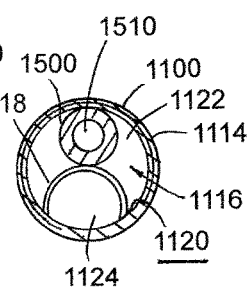
FIG. 4C is an enlarged sectional view of the first example catheter assembly, taken along line 4C-4C in FIG. 4A.
Figure 4D:
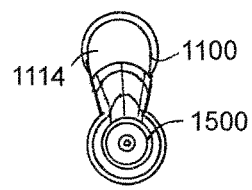
FIG. 4D is an distal end view of the first example catheter assembly.

The main body 1170 is disposed between the proximal 1130 and distal 1150 portions. As best illustrated in FIG. 4C, the main body 1170 contains both the drainage 1122 and infusion 1124 lumens. Also, as best illustrated in FIG. 3, the main body 1170 has an outer diameter $x_1$ that is substantially uniform along the axial length of the main body 1170. Each of the lumens in a catheter according to a particular embodiment can have any suitable size and cross-sectional shape, and a skilled artisan will be able to select an appropriate size and cross-sectional shape for a catheter according to a particular embodiment based on various considerations, including the size and shape of any introducer intended to be used with the catheter and the body location within which the catheter is intended to be used. Examples of suitable cross-sectional shapes for each of the lumens in a catheter according to an embodiment include, but are not limited to, reniform and semi-circular cross-sectional shapes. The inventors have determined that the drainage lumen advantageously has a reniform cross-sectional shape, such as the reniform cross-sectional shape of the drainage lumen 1122 illustrated in FIG. 4C. As a reniform shape, the drainage lumen is bounded by a substantially circular outer arc defined by the circumferential wall 1114 and a substantially circular inner arc defined by the septum 1118. The outer and inner arcs interface with each other at lateral junctions disposed adjacent the infusion lumen 1124. Each of the junctions can have any suitable configuration, including angled and rounded corners, such as the rounded corners illustrated in FIG. 4C. If angled corners are included, any suitable angle can be used, but acute angles are considered advantageous. If rounded corners are included, any suitable rounded corner can be used. The inventors have determined, though, that rounded corners having a radius that is greater than about 10% of the largest circular cross-sectional shape that can be inscribed within the reniform cross-sectional shape of the drainage lumen 1122. This relative sizing of the lumen and rounded corners is considered advantageous at least because it provides desirable structural characteristics for the catheter 1100, septum 1118, and lumens 1122, 1124.

The proximal end 1152 of the distal portion 1150 defines distal extension 1154 that has an outer diameter $x_2$ that is substantially uniform along the axial length of the distal extension 1154. Similarly, the distal end 1156 of the distal portion defines distal tip 1158 that has an outer diameter $x_3$ that is substantially uniform along the axial length of the distal tip 1158. As best illustrated in FIG. 3, outer diameter $x_3$ is less than outer diameter $x_2$, which is less than outer diameter $x_1$. As a result, distal portion 1150 includes first 1160 and second 1162 tapered portions. The outer diameter of the catheter 1100 tapers from outer diameter $x_1$ to outer diameter $x_2$ along the length of the first tapered portion 1160. Similarly, the outer diameter of the catheter 1100 tapers from outer diameter $x_2$ to outer diameter $x_3$ along the length of the second tapered portion 1162.

The distal tip in a catheter according to a particular embodiment can have any suitable size and configuration, and a skilled artisan will be able to select an appropriate size and configuration for a catheter according to a particular embodiment based on various considerations, including the body location within which the catheter is intended to be used. Examples of suitable configurations for the distal tip in a catheter according to an embodiment include, but are not limited to, straight, such as the distal tip 1158 in the illustrated embodiment, and curved. If a curved distal tip is used in a catheter according to a particular embodiment, the curved distal tip can define any suitable curve, include a j-curve, a partial j-curve, and any other suitable curve. Septum 1118 divides the internal lumen 1116 into a drainage lumen and 1122 and an infusion lumen 1124. As best illustrated in FIG. 4C, septum 1118 extends inwardly from and is continuous with the internal surface 1120 of the circumferential wall 1114. Thus, also as best illustrated in FIG. 4C, both the drainage lumen 1122 and infusion lumen 1124 are cooperatively defined by the internal surface 1120 of the circumferential wall 1114 and the septum 1118. Septum 1118 extends between the infusion port 1124 at the bifurcation 1140 and infusion opening 1180 defined by the circumferential wall 1114. Infusion opening 1180 is a passageway through the thickness of the circumferential wall 1114 that places the infusion lumen 1124 in fluid communication with the environment external to the catheter 1100. Thus, the infusion lumen 1124 extends between the infusion opening 1180 and the infusion port 1134.

The circumferential wall 1114 defines a first set of drainage openings 1190 in the main body 1170. Each opening of the first set of drainage openings 1190 is a passageway through the thickness of the circumferential wall 1114 that places the drainage lumen 1124 in fluid communication with the environment external to the catheter 1100. In the illustrated embodiment, the circumferential wall 1114 defines a second set of drainage openings 1192 in the distal tip 1158. Thus, as best illustrated in FIG. 4A, drainage lumen 1122 extends between the distal opening 1194 defined by the distal end 1112 of the catheter and the drainage port 1132 and the openings of the first 1190 and second 1192 sets of drainage openings provide supplemental lateral access to the drainage lumen 1122.

One or more sets of drainage openings can be positioned at any suitable position along the axial length of a catheter according to a particular embodiment, and the illustrated axial positions of the first 1190 and second 1192 sets of drainage openings are examples of suitable positions. It is noted, though, that, in the illustrated embodiment, the first set of drainage openings 1190 is positioned proximal to the infusion opening 1180 along the axial length of the catheter 1100 while the second set of drainage openings 1192 is positioned distal to the infusion opening 1180 along the axial length of the catheter 1100. This positioning is considered advantageous at least because it facilitates drainage from a patient during ECMO by enabling positioning of the first set of drainage openings 1190 in the superior vena cava of the patient and positioning of the second set of draining openings 1192 in the inferior vena cava of the patient, with simultaneous infusion into the right atrium of the patient through the infusion opening 1180.

Figure 1:
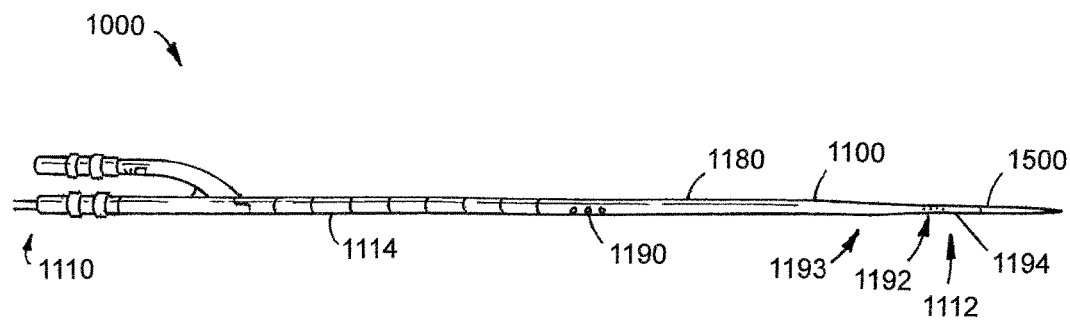
FIG. 1 is a perspective view of a first example catheter assembly.
Figure 2:
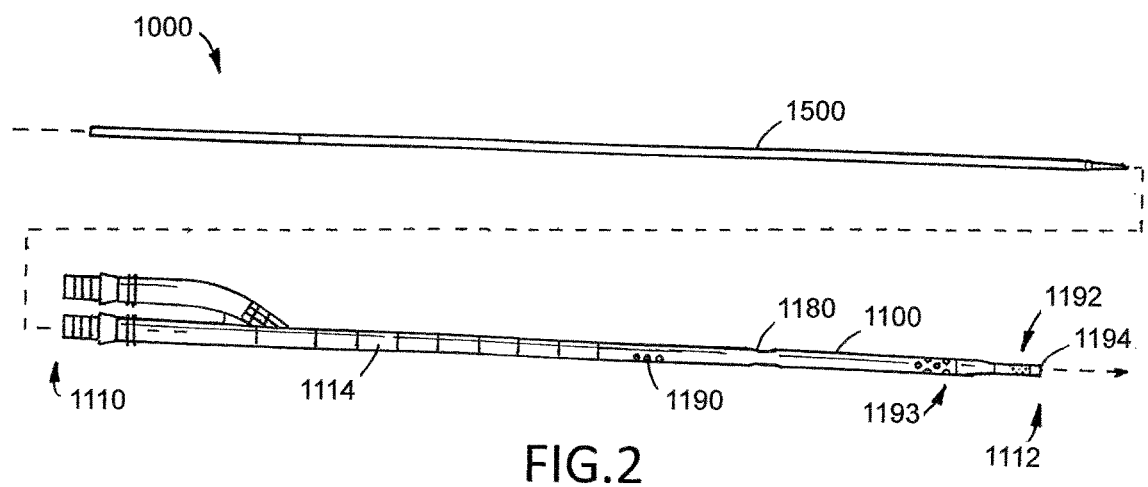
FIG. 2 is an exploded view of the first example catheter assembly.

While the illustrated embodiment includes a second set of drainage openings 1192, this is considered optional and a catheter according to a particular embodiment can contain only a single set of drainage openings. Furthermore, a catheter according to a particular embodiment can include additional sets of drainage openings. For example, as best illustrated in FIGS. 1 through 3, a third set of drainage openings 1193 can be positioned in the distal portion 1150 of the catheter 1100, such as in distal extension 1154.

Each set of drainage openings can include various numbers of openings, and a skilled artisan will be able to select a suitable number of openings for each set of drainage openings in a catheter according to a particular embodiment based on a variety of considerations. Furthermore, each set of drainage openings can be positioned circumferentially on the catheter in various arrangements and a skilled artisan will be able to select a suitable circumferential arrangement for each set of drainage openings in a catheter according to a particular embodiment based on a variety of considerations. The inventors have determined that certain numbers and circumferential arrangements provide advantages, though. For example, in the illustrated embodiment, the first set of drainage openings 1190 comprises three openings that are extend only partially around the circumference of the catheter 1100. That is, the first set of drainage openings extends along only a portion of the circumference of the catheter 1100. In contrast, in this embodiment, the second set of drainage openings comprises a greater number of openings than the first set and the second set of openings extends completely around the circumference of the catheter 1100. That is, the second set of drainage openings extends along the entire circumference of the catheter 1100. These numbers and circumferential arrangements of openings in the first 1190 and second 1192 sets of drainage openings is considered advantageous at least because they cooperate with other structural features of the catheter to provide beneficial performance characteristics. Also, as best illustrated in FIGS. 1 through 3, it is considered advantageous to position the first set of drainage openings 1190 on the portion of the circumferential wall 1114 that is opposite, or substantially opposite, the infusion opening 1180 of the catheter. This positioning is considered advantageous at least because it reduces the possibility that fluid exiting the infusion opening 1180 will immediately enter the openings of the first set of drainage openings 1190.

Figure 4E:
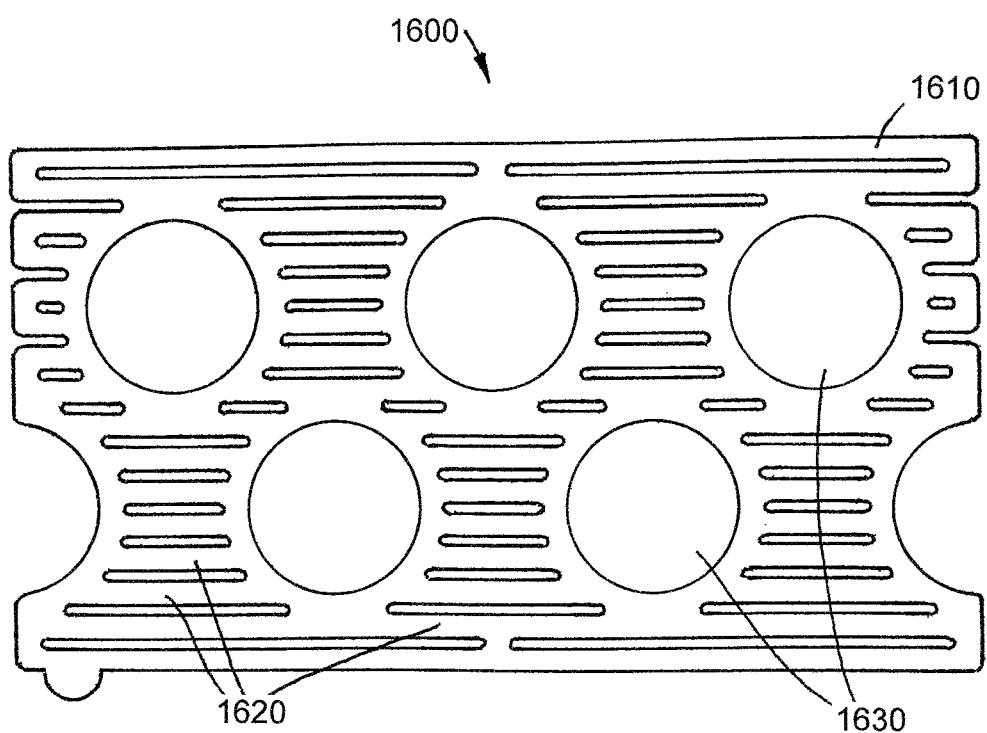
FIG. 4E is a flat plan view of the reinforcement band of the first example catheter assembly.
Figure 5:
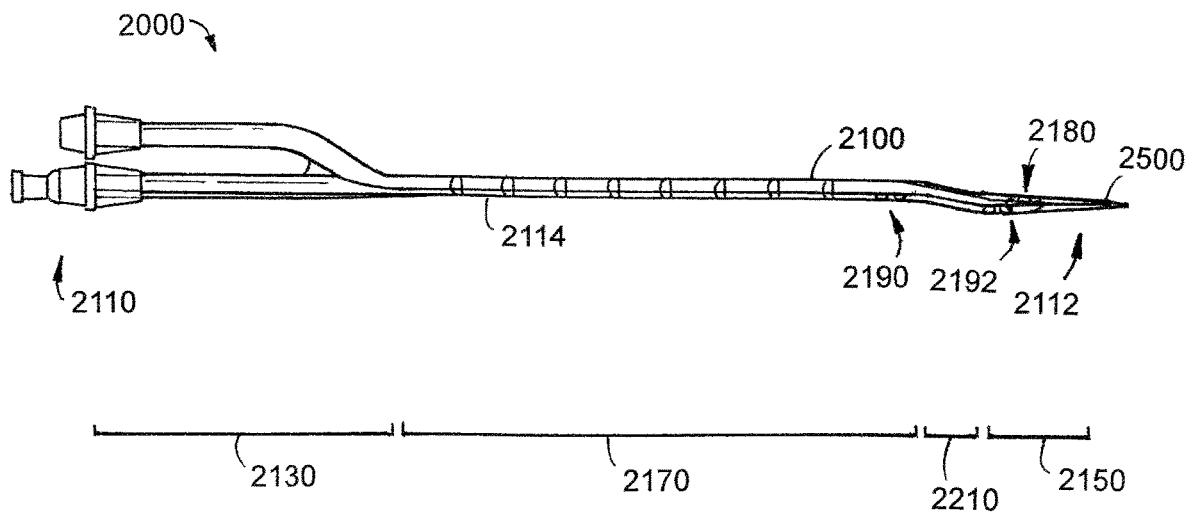
FIG. 5 is a side view of a second example catheter assembly.

A catheter according to a particular embodiment can include one or more reinforcement bands, if desired. For example, catheter 1100 includes reinforcement band 1600 disposed in the distal extension 1154. In the illustrated embodiment, reinforcement band 1600 is a metal lattice 1610 disposed within the thickness of the circumferential wall 1114 of the catheter 1100. Any suitable reinforcement band can be used in a catheter according to a particular embodiment, and a skilled artisan will be able to select an appropriate reinforcement band for a particular catheter based on various considerations, including any desired flexibility, structure for drainage openings, etc. As best illustrated in FIG. 4E, the reinforcement band 1600 in this embodiment is a metal lattice 1610 having a plurality of ribs 1620 and defining a plurality of ports 1630. Each port of the plurality of ports 1630 is substantially circular in shape and, in the assembled catheter 1100, is aligned with a drainage opening of the first set of drainage openings 1190. Additional reinforcement bands can be included in a catheter according to a particular embodiment, if desired.

Introducer 1500 is an elongate member that is slidably disposed within the drainage lumen 1122 of catheter 1100. The introducer 1500 defines a wireguide lumen 1510 through which a conventional wireguide can be passed to facilitate navigation of the introducer 1500, and catheter assembly 1000, through a body vessel. To facilitate initial entry into a body vessel, introducer 1500 defines a tapered distal end 1520.

Figure 6:
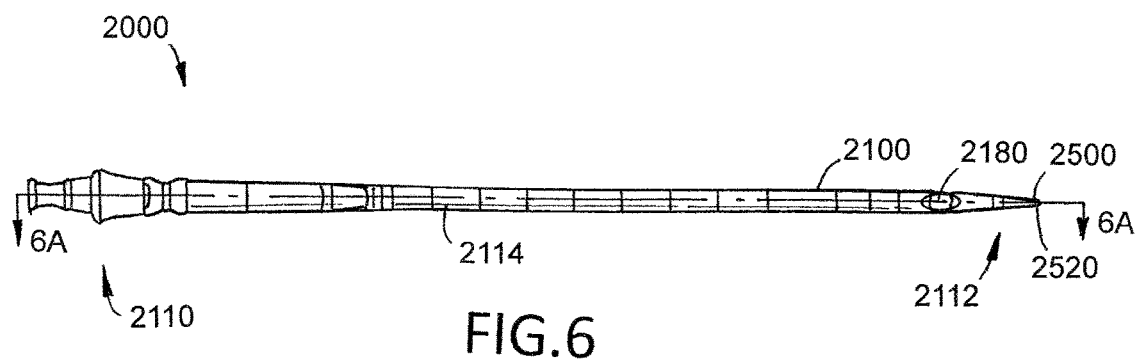
FIG. 6 is a top view of the second example catheter assembly.
Figure 6A:
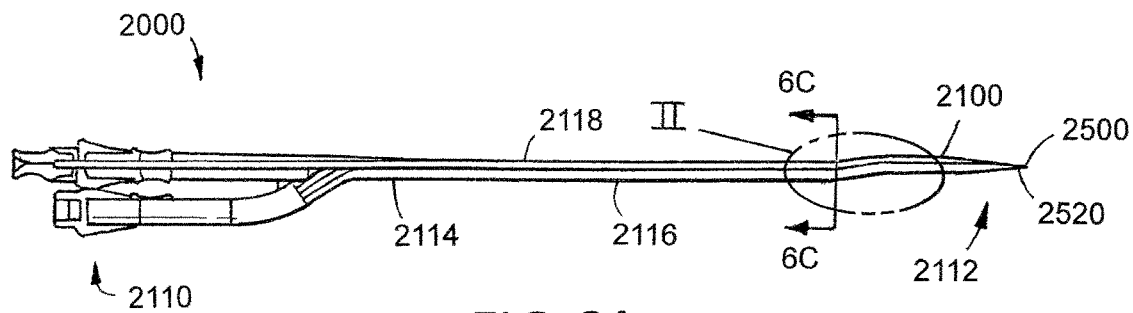
FIG. 6A is a sectional view of the second example catheter assembly, taken along line 6A-6A in FIG. 4.
Figure 6B:
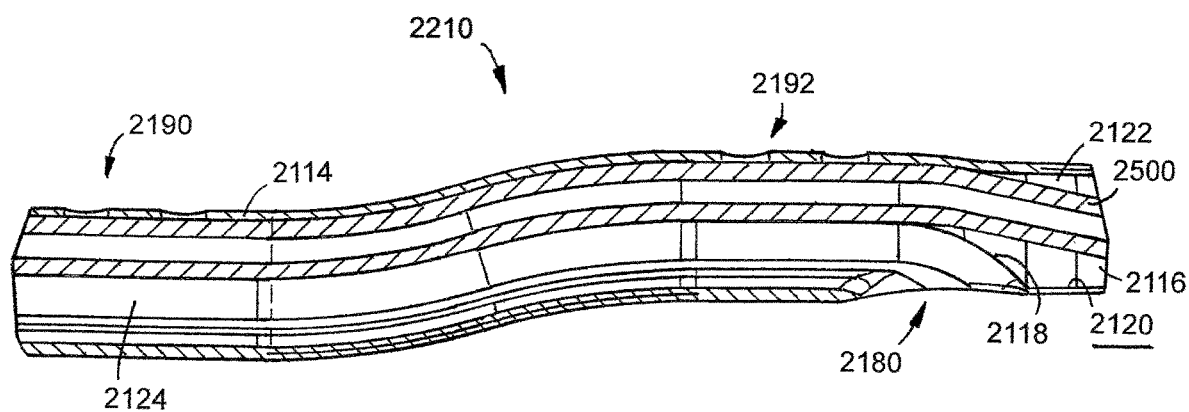
FIG. 6B is an enlarged sectional view of area II in FIG. 6A.
Figure 6C:
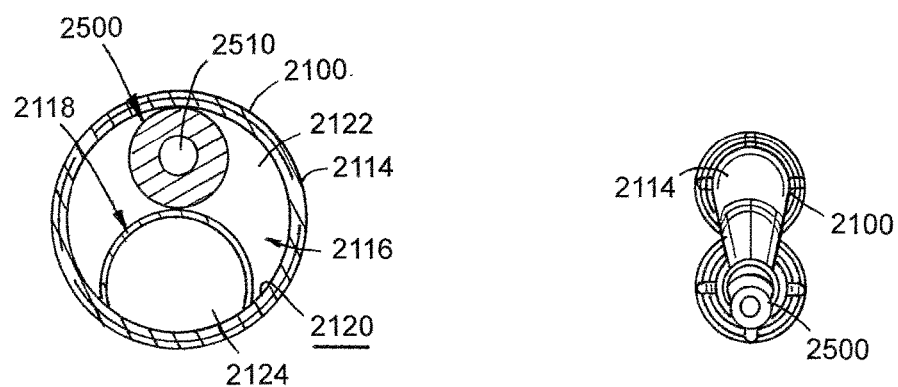
FIG. 6C is an enlarged sectional view of the second example catheter assembly, taken along line 6C-6C in FIG. 6A.
Figure 6D:
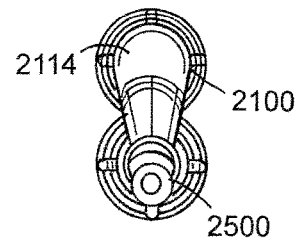
FIG. 6D is an distal end view of the second example catheter assembly.
Figure 7:
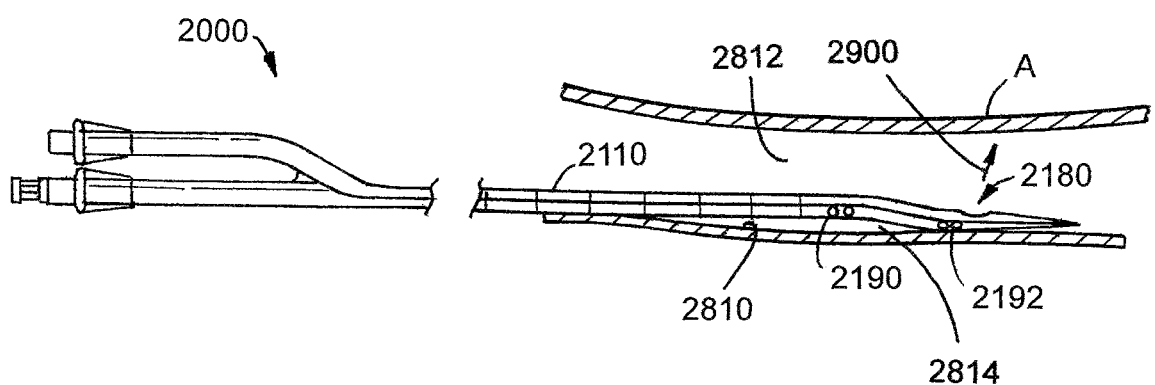
FIG. 7 is a sectional view of a portion of a body vessel within which the second example catheter assembly is disposed. The catheter assembly is partially broken away for illustration purposes.
Figure 8:
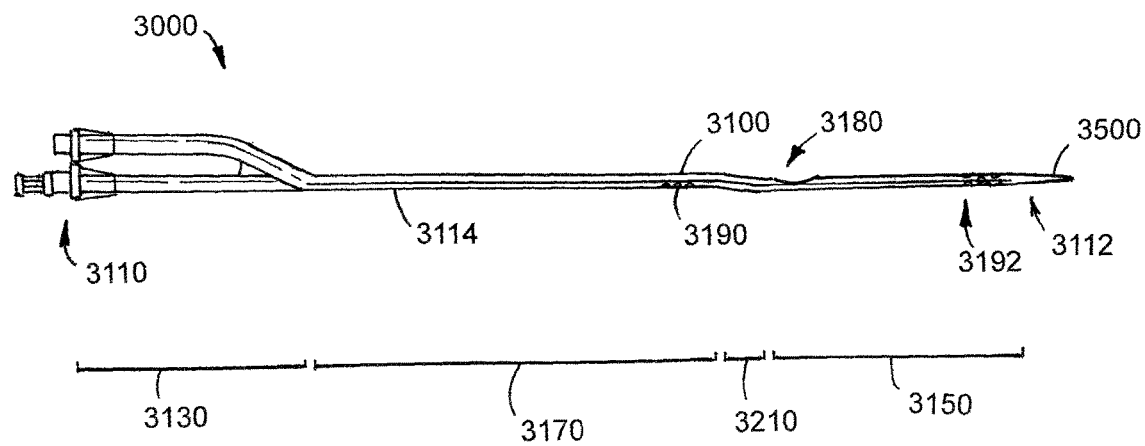
FIG. 8 is a side view of a third example catheter assembly.
Figure 9:
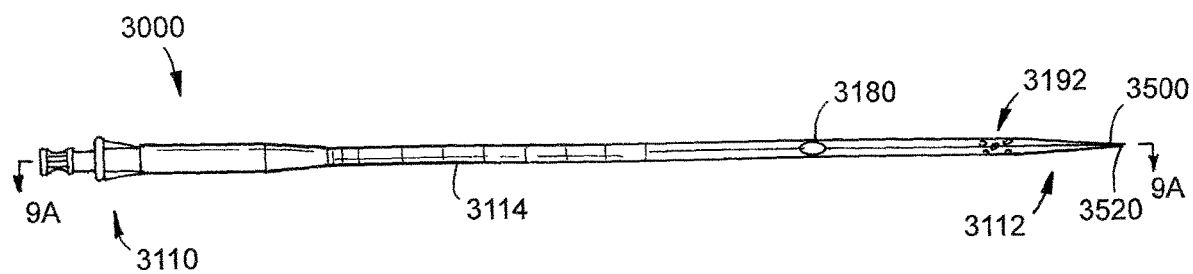
FIG. 9 is a top view of the third example catheter assembly.
Figure 9A:
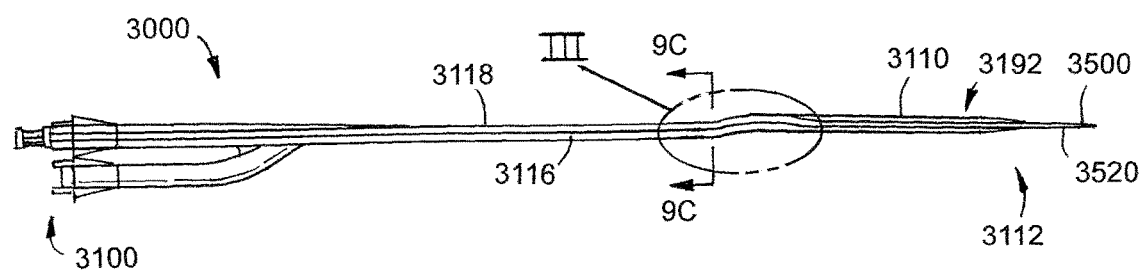
FIG. 9A is a sectional view of the third example catheter assembly, taken along line 9A-9A in FIG. 9.

FIGS. 5, 6, 6A, 6B, 6C, and 6D illustrate a second example catheter assembly 2000. The catheter assembly 2000 includes catheter 2100 and introducer 2500. FIG. 7 illustrates the second example catheter assembly 2000 disposed within a body vessel A.

Catheter 2100 is similar to catheter 1100 described above, except as detailed below. Thus, catheter 2100 is an elongate member that extends from a proximal end 2110 to a distal end 2112. A circumferential wall 2114 extends between the proximal 2110 and distal 2112 ends and defines an internal lumen 2116. A septum 2118 extends inwardly from the internal surface 2120 of the circumferential wall 2114 and divides the internal lumen 2114 into a drainage 2122 lumen and an infusion lumen 2124. A proximal portion 2130 extends distally from the proximal end 2110 and toward the distal end 2112. A distal portion 2150 extends proximally from the distal end 2112 and toward the proximal end 2110. A main body 2170 is disposed between the proximal 2130 and distal 2150 portions. The proximal portion 2130 includes drainage port 2132 and infusion port 2134. The drainage port 2132 is in fluid communication with the drainage lumen 2122 while infusion port 2134 is in fluid communication with the infusion lumen 2124. A first connector 2136 is disposed on the drainage port 2132 and a second connector 2138 is disposed on the infusion port 2134. The circumferential wall defines an infusion opening 2180 that places the infusion lumen 2124 in fluid communication with the environment external to the catheter 2100. Thus, the infusion lumen 2124 extends between the infusion opening 2180 and the infusion port 2134. The circumferential wall 2114 also defines a first set of drainage openings 2190 in the main body 2170 and a second set of drainage openings 2192 in the distal portion 2150. Drainage lumen 2122 extends between the distal opening 2194 defined by the distal end 2112 of the catheter 2100 and the drainage port 2132 and the openings of the first 2190 and second 2192 sets of drainage openings provide supplemental lateral access to the drainage lumen 2122. Drainage lumen 2122 has a reniform cross-sectional shape bounded by an outer arc defined by the circumferential wall 2114 and an inner arc defined by the septum 2118 that interface with each other at lateral junctions comprising rounded corners disposed adjacent the infusion lumen 2124.

In this embodiment, the distal portion 2150 and main body 2170 of the catheter 2100 have different longitudinal axes that are substantially parallel to each other. Furthermore, catheter 2100 defines offset portion 2210 that transitions between the main body 2170 and distal 2150 portions. With this structural arrangement, offset portion 2210 defines a curve that transitions between the main body 2170 and the distal portion 2150. As best illustrated in FIG. 6B, the infusion opening 2180 and first set of drainage openings 2190 are positioned on opposite inside portions of the curve of the offset portion 2210.

Also in this embodiment, the infusion opening 2180 is disposed axially distal to both the first set of drainage openings 2190 and the second set of drainage openings 2192. This positioning is considered advantageous at least because it facilitates drainage from the superior vena cava of a patient through both sets 2190, 2192 of drainage openings during ECMO with simultaneous infusion into the right atrium of the patient through the infusion opening 2180. Also in this embodiment, each of the first 2190 and second 2192 sets of drainage openings extends along only a portion of the circumference of the catheter 2100 at the respective location of each set 2190, 2192 of drainage openings. Furthermore, each of the first 2190 and second 2192 sets of drainage openings is positioned substantially on the opposite side of the circumfential wall 2114 relative to the position of the infusion opening 2180 and the longitudinal axis of the catheter 2100. As best illustrated in FIG. 7, this positioning, along with the inclusion of the offset portion 2210, ensures spacing from the interior wall 2810 of a body vessel A as the force of fluid, such as blood, represented by arrow 2900, exiting through the infusion opening 2180 pushes the catheter 2100 against the interior wall 2810 of the body vessel A. This spacing, which is achieved by the inclusion of the offset portion 2210, decreases the likelihood that the openings of the first set of drainage openings 2190 become obstructed through contact with the interior wall 2810 that occurs as the catheter 2100 is pushed against the interior wall 2810 of the body vessel A in response to fluid represented by arrow 2900 exiting the infusion opening 2180. As best illustrated in FIG. 7, the offset portion 2210 creates a void 2814 between the first set of drainage openings 2190 and the interior wall 2810 of the body vessel A. Furthermore, the partial circumferential arrangement of the first 2190 and second 2192 sets of drainage openings is considered particularly advantageous in embodiments in which the infusion opening is positioned axially distal to both the first set of drainage openings and the second set of drainage openings at least because it reduces the possibility that fluid exiting the infusion opening will immediately enter the openings of either the first set of drainage openings or the second set of drainage openings.

Figure 6E:
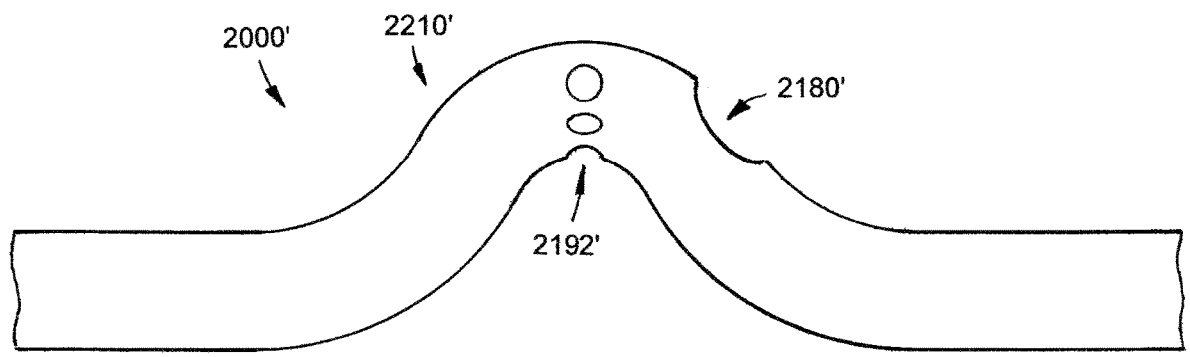
FIG. 6E is a side view, partially broken away, of the main body of an alternative catheter.

FIG. 6E illustrates the main body 2170', offset portion 2210', and distal portion 2150' of an alternate catheter 2000'. In this embodiment, the offset portion 2210' defines a u-shaped curve between the main body 2170' and distal portion 2150'. The infusion opening 2180' is disposed on the outside of the u-shaped curve of the offset portion 2210', toward the distal portion 2150'. Also, the first set of drainage openings 2190' is disposed on the inside of the u-shaped curve of the offset portion 2210'. With this structural arrangement, the overall volume of the void created between the offset portion 2210' and the inner surface of the wall of a body vessel within which the catheter is positioned is reduced but the first set of drainage openings 2190' remains spaced from the inner surface as in the catheter 2000 described above. As such, this structural arrangement achieves the desired decrease in likelihood that the openings of the first set of drainage openings 2190 become obstructed through contact with the interior wall of a body vessel within which the catheter 2000' is positioned as the catheter 2000' is pushed against the interior wall of the body vessel in response to fluid exiting the infusion opening 2180. This structural arrangement may be advantageous for catheters for which it is desirable to limit the spacing of the first set of drainage openings from a body vessel wall to a relatively short axial length of the catheter.

Introducer 2500 is similar to introducer 1500 described above. Thus, introducer 2500 is an elongate member that is slidably disposed within the drainage lumen 2122 of catheter 2100. The introducer 2500 defines a wireguide lumen 2510 through which a conventional wireguide can be passed to facilitate navigation of the introducer 2500, and catheter assembly 2000, through a body vessel. To facilitate initial entry into a body vessel, introducer 2500 defines a tapered distal end 2520.

Figure 10:
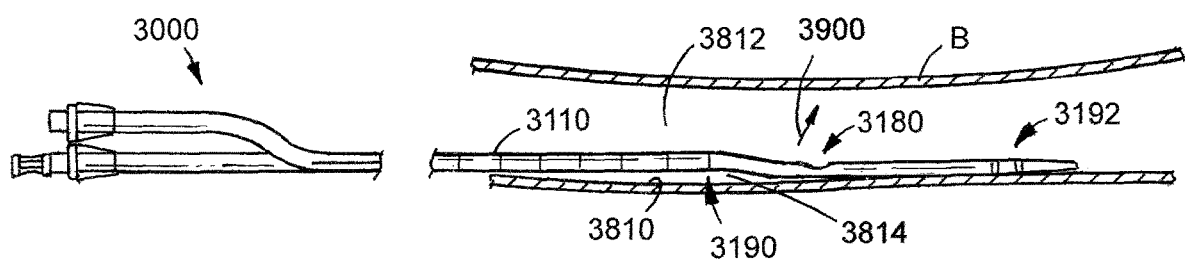
FIG. 10 is a sectional view of a portion of a body vessel within which the third example catheter assembly is disposed. The catheter assembly is partially broken away for illustration purposes.

FIGS. 8, 9, 9A, 9B, 9C, and 9D illustrate a third example catheter assembly 3000. The catheter assembly 3000 includes catheter 3100 and introducer 3500. FIG. 10 illustrates the third example catheter assembly 3000 disposed within a body vessel B.

Catheter 3100 is similar to catheter 2100 described above, except as detailed below. Thus, catheter 3100 is an elongate member that extends from a proximal end 3110 to a distal end 3112. A circumferential wall 3114 extends between the proximal 3110 and distal 3112 ends and defines an internal lumen 3116. A septum 3118 extends inwardly from the internal surface 3120 of the circumferential wall 3114 and divides the internal lumen 3114 into a drainage 3122 lumen and an infusion lumen 3124. A proximal portion 3130 extends distally from the proximal end 3110 and toward the distal end 3112. A distal portion 3150 extends proximally from the distal end 3112 and toward the proximal end 3110. A main body 3170 is disposed between the proximal 3130 and distal 3150 portions. The proximal portion 3130 includes drainage port 3132 and infusion port 3134. The drainage port 3132 is in fluid communication with the drainage lumen 3122 while infusion port 3134 is in fluid communication with the infusion lumen 3124. A first connector 3136 is disposed on the drainage port 3132 and a second connector 3138 is disposed on the infusion port 3134. The circumferential wall defines an infusion opening 3180 that places the infusion lumen 3124 in fluid communication with the environment external to the catheter 3100. Thus, the infusion lumen 3124 extends between the infusion opening 3180 and the infusion port 3134. The circumferential wall 3114 also defines a first set of drainage openings 3190 in the main body 3170 and a second set of drainage openings 3192 in the distal portion 3150. Drainage lumen 3122 extends between the distal opening 3194 defined by the distal end 3112 of the catheter 3100 and the drainage port 3132 and the openings of the first 3190 and second 3192 sets of drainage openings provide supplemental lateral access to the drainage lumen 3122. Drainage lumen 3122 has a reniform cross-sectional shape bounded by an outer arc defined by the circumferential wall 3114 and an inner arc defined by the septum 3118 that interface with each other at lateral junctions comprising rounded corners disposed adjacent the infusion lumen 3124.

In this embodiment, the distal portion 3150 and main body 3170 of the catheter 3100 have different longitudinal axes that are substantially parallel to each other. Furthermore, catheter 3100 defines offset portion 3210 that transitions between the main body 3170 and distal 3150 portions. With this structural arrangement, offset portion 3210 defines a curve that transitions between the main body 3170 and the distal portion 3150. As best illustrated in FIG. 9B, the infusion opening 3180 and first set of drainage openings 3190 are positioned on opposite inside portions of the curve of the offset portion 3210.

Also in this embodiment, the infusion opening 3180 is disposed axially between the first set of drainage openings 3190 and the second set of drainage openings 3192. Furthermore, the first set of drainage openings 3190 is axially spaced from the infusion opening by a first distance and the second set of drainage openings is axially spaced from the infusion opening by a second distance that is greater than the first distance. This positioning is considered advantageous at least because it facilitates drainage from both the superior vena cava and the inferior vena cava of a patient through the first set of drainage openings 3190 and the second set of drainage openings 3192, respectively, during ECMO with simultaneous infusion into the right atrium of the patient through the infusion opening 3180. As such, the catheter 3100 is particularly well-suited for use as a bicaval catheter during ECMO or other extracorporeal circulation. Also in this embodiment, the first set of drainage openings 3190 extends along only a portion of the circumference of the catheter and is positioned substantially on the opposite side of the circumfential wall 3114 relative to the position of the infusion opening 3180. The second set of drainage openings 3192 extends around the entire circumference of the distal portion 3150 of the catheter 3100. As best illustrated in FIG. 10, this positioning, along with the inclusion of the offset portion 3210, ensures that the first set of drainage openings 3190 are spaced from the interior wall 3810 of a body vessel B as the force of fluid, such as blood, represented by arrow 3900, exiting through the infusion opening 3180 pushes the catheter 3100 against the interior wall 3810 of the body vessel B. This spacing, which is achieved by the inclusion of the offset portion 3210, decreases the likelihood that the openings of the first set of drainage openings 3190 become obstructed through contact with the interior wall 3810 that occurs as the catheter 3100 is pushed against the interior wall 3810 of the body vessel B in response to fluid represented by arrow 3900 exiting the infusion opening 3180. As best illustrated in FIG. 10, the offset portion 3210 creates a void 3814 between the first set of drainage openings 3190 and the interior wall 3810 of the body vessel B. Also, in this embodiment, because the second set of drainage openings 3192 extends completely circumferentially around the distal portion 3150 of the catheter 3100, some of the openings of the second set of drainage openings 3192 are not obstructed through such contact with the interior wall 3810 of the body vessel B. As such, even though the distal portion 3150 of the catheter 3100 may be pushed toward the interior wall 3810 of the body vessel, drainage can still occur through the second set of drainage openings 3192 because the openings of the second set of drainage openings 3192 that are positioned toward the lumen 3812 of the body vessel B will not be obstructed by such contact. This partial circumferential arrangement of the first set of drainage openings 3190 and full circumferential arrangement of the second set of drainage openings 3192 is considered particularly advantageous in embodiments in which the infusion opening is positioned axially between the first set of drainage openings and the second set of drainage openings and in which the second set of drainage openings is axially spaced a distance from the infusion opening that is greater than a distance by which the first set of drainage openings is axially spaced from the infusion opening.

Introducer 3500 is similar to introducer 1500 described above. Thus, introducer 3500 is an elongate member that is slidably disposed within the drainage lumen 3122 of catheter 3100. The introducer 3500 defines a wireguide lumen 3510 through which a conventional wireguide can be passed to facilitate navigation of the introducer 3500, and catheter assembly 3000, through a body vessel. To facilitate initial entry into a body vessel, introducer 3500 defines a tapered distal end 3520.

Figure 11A:
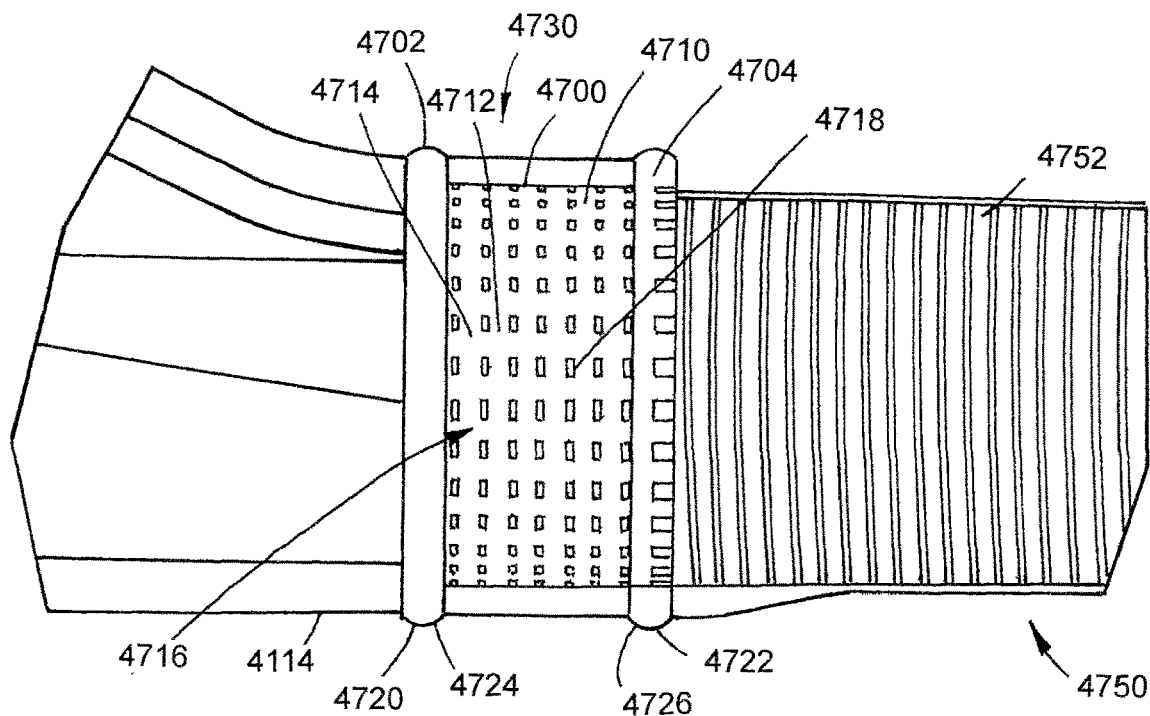
FIG. 11A is an enlarged sectional view of area IV in FIG. 11.

FIGS. 11, 11A, and 12 illustrate another example catheter 4100. Catheter 4100 is similar to catheter 1100 described above, except as detailed below. Thus, catheter 4100 is an elongate member that extends from a proximal end 4110 to a distal end 4112. A circumferential wall 4114 extends between the proximal 4110 and distal 4112 ends and defines an internal lumen. A septum extends inwardly from the internal surface of the circumferential wall and divides the internal lumen into a drainage lumen and an infusion lumen. A proximal portion 4130 extends distally from the proximal end 4110 and toward the distal end 4112. A distal portion 4150 extends proximally from the distal end 4112 and toward the proximal end 4110. A main body 4170 is disposed between the proximal 4130 and distal 4150 portions. The proximal portion 4130 includes drainage port 4132 and infusion port 4134. The drainage port 4132 is in fluid communication with the drainage lumen while infusion port 4134 is in fluid communication with the infusion lumen. A first connector 4136 is disposed on the drainage port 4132 and a second connector 4138 is disposed on the infusion port 4134. The circumferential wall defines an infusion opening 4180 that places the infusion lumen in fluid communication with the environment external to the catheter 4100. Thus, the infusion lumen extends between the infusion opening 4180 and the infusion port 4134. The circumferential wall 4114 also defines a first set of drainage openings 4190 in the main body 4170 and a second set of drainage openings 4192 in the distal portion 4150. Drainage lumen extends between the distal opening 4194 defined by the distal end 4112 of the catheter 4100 and the drainage port 4132 and the openings of the first 4190 and second 4192 sets of drainage openings provide supplemental lateral access to the drainage lumen 4122.

Figure 13:
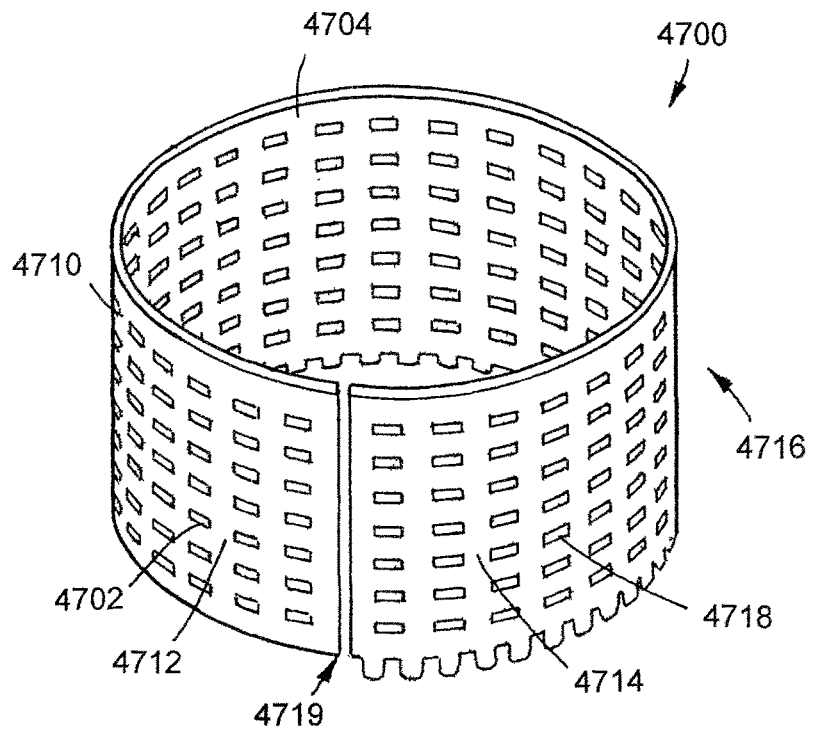
FIG. 13 is a perspective view of an example reinforcement band.

In this embodiment, a reinforcement mesh 4700 is embedded in the circumferential wall 4114 in the main body 4170 of the catheter 4100. As best illustrated in FIG. 13, the reinforcement mesh 4700 has a proximal end 4702 and a distal end 4704. The reinforcement mesh 4700 is a partial ring structure 4710 that includes a series of parallel circumferential members 4712 joined together with a series of parallel axial members 4714 to form a mesh 4716 having a plurality of regularly spaced and sized openings 4718. A longitudinal slit 4719 is disposed on one side of the ring structure 4710.

As best illustrated in FIG. 11A, the reinforcement mesh 4700 is embedded in the circumferential wall 4114 of the main body of the catheter 4100. A first annular ring 4720 is embedded within the circumferential wall 4114 radially outward of the proximal end 4702 of the reinforcement mesh 4700, and a second annular ring 4722 is embedded within the circumferential wall 4114 radially outward of the distal end 4704 of the reinforcement mesh 4700. These annular rings 4720, 4722 form annular bumps 4724, 4726 in the circumferential wall 4114 above both ends 4702, 4704 of the reinforcement mesh 4700.

The reinforcement mesh 4700, along with the annular rings 4720, 4722, creates a reinforced circumferential channel 4730 on the outer surface of the circumferential wall 4114, providing an axial position on the length of the catheter 4100 around which a user can secure a suture or other connector to the catheter 4100. The presence of the axial members 4714 prevent sutures placed around the reinforcement mesh 4700 from passing into the spaces between the circumferential members 4712, which, ultimately, prevents restriction of the catheter lumen. The annular rings 4720, 4722, and the associated annular bumps 4724, 4726 prevent sutures placed around the reinforcement mesh 4700 from moving axially along the length of the catheter 4100, onto a non-reinforced section of the circumferential wall 4114 or to a section of the circumferential wall 4114 having a helical reinforcement, such as section 4750 with helical reinforcement member 4752.

If included in a catheter according to a particular embodiment, a reinforcement mesh and annular rings can be formed of any suitable material or materials that provide the desired resistance to restriction on the catheter lumen by sutures secured around the reinforcement mesh. Metals and alloys are considered particularly well suited for the reinforcement mesh. Furthermore, while the illustrated embodiment includes annular rings that are members separate from the reinforcement mesh, it is noted that a reinforcement mesh can integrally form one or both annular rings. This structural arrangement may provide manufacturing advantages. Also, while the illustrated embodiment includes only a single reinforcement mesh, a catheter according to a particular embodiment can include additional reinforcement meshes, and annular rings, placed along the axial length of the catheter at locations at which it may be desirable to secure sutures around the catheter. Examples of contemplated numbers of reinforcement meshes that can be included in a catheter according to a particular embodiment include two, three, a plurality, and more than three reinforcement meshes.

FIGS. 14, 15, 16A, 16B, 16C, 16D, 16E, 16F, 16G, 16H, 16I, 16J, 16K, 16L, and 16M illustrate another example catheter 5100. Catheter 5100 is similar to catheter 1100 described above, except as detailed below. Thus, catheter 5100 is an elongate member that extends from a proximal end 5110 to a distal end 5112. A circumferential wall 5114 extends between the proximal 5110 and distal 5112 ends and defines an internal lumen. A septum extends inwardly from the internal surface of the circumferential wall and divides the internal lumen into a drainage lumen and an infusion lumen. A proximal portion 5130 extends distally from the proximal end 5110 and toward the distal end 5112. A distal portion 5150 extends proximally from the distal end 5112 and toward the proximal end 5110. A main body 5170 is disposed between the proximal 5130 and distal 5150 portions. The proximal portion 5130 includes drainage port 5132 and infusion port 5134. The drainage port 5132 is in fluid communication with the drainage lumen while infusion port 5134 is in fluid communication with the infusion lumen. A first connector 5136 is disposed on the drainage port 5132 and a second connector 5138 is disposed on the infusion port 5134. The circumferential wall 5114 defines an infusion opening 5180 that places the infusion lumen in fluid communication with the environment external to the catheter 5100. Thus, the infusion lumen extends between the infusion opening 5180 and the infusion port 5134. The circumferential wall 5114 also defines a first set of drainage openings 5190 in the main body 5170 and a second set of drainage openings 5192 in the distal portion 5150. Drainage lumen 5122 extends between the distal opening 5194 defined by the distal end 5112 of the catheter 5100 and the drainage port 5132 and the openings of the first 5190 and second 5192 sets of drainage openings provide supplemental lateral access to the drainage lumen 5122.

In this embodiment, a series of radiographic markers 5800 is embedded in the circumferential wall 5114 in the main body 5170 of the catheter 5100, proximal and adjacent to the infusion opening 5180. The series of radiographic markers 5800 enables a user of the catheter 5100 to visualize the catheter 5100 during use using fluoroscopy or ultrasound imaging technology and equipment. Imaging with conventional catheters has proven difficult to determine the orientation of the catheter within the vessel. The inventors have determined that the catheters described herein will operate most efficiently and effectively when fluid flow exiting the infusion opening 5180 is directed toward the tricuspid valve of the heart of a patient within which the catheter is placed. The series of radiographic markers 5800 facilitate achievement of this desired orientation by providing an asymmetrical pattern that allows the orientation to be determined.

As best illustrated in FIGS. 16B and 16L, the series of radiographic markers 5800 comprises three radiographic markers, such as tantalum disks or other suitable markers, embedded in the circumferential wall 5114 of the catheter 5100. Two of the markers 5802, 5804 are aligned on a longitudinal, axial line on the circumferential wall 5114 of the catheter 5100. The third marker 5806 is aligned with one of the first 5802 and second 5804 markers on a circumferential line on the circumferential wall 5114 of the catheter 5100. The circumferential line orthogonally surrounds the longitudinal axis of the main body 5170 of the catheter 5100. As such, as best illustrated in FIG. 16D, a first subset of the series of radiographic markers 5800 comprises an even number of radiographic markers and is disposed on a first axial side of the infusion opening 5180, while a second subset of the series of radiographic markers 5800 comprises an odd number of radiographic markers and is disposed on a second, opposite axial side of the infusion opening 5180. This asymmetrical pattern of the series of radiographic markers 5800 allows the orientation of the adjacent infusion port 5180 to be determined when the catheter 5100 is viewed from the side under fluoroscopy, ultrasound, or others suitable imaging equipment and technology.

As best illustrated in FIGS. 16B, 16C, 16D, 16E, 16F, and 16G, the infusion opening 5180, and therefore the direction of fluid flow exiting the infusion opening 5180, represented by arrow 5808, is directed up, toward the front of the patient within which the catheter 5100 is positioned, when the first 5802 and second 5804 markers are positioned, and visible under imaging, to the left of the third marker 5806. In contrast, as best illustrated in FIGS. 16H, 16I, 16J, 16K, and 16L, the infusion opening 5180, and therefore the direction of fluid flow exiting the infusion opening 5180, represented by arrow 5808, is directed down, toward the back of the patient within which the catheter 5100 is positioned, and visible under imaging, when the first 5802 and second 5804 markers are positioned to the right of the third marker 5806. In FIGS. 16A, 16G, and 16M, infusion opening 5180, and, therefore, the direction of fluid flow exiting the infusion opening 5180, represented by arrow 5808, is directed laterally toward one or the other sides of the patient within which the catheter 5100 is positioned, when only the first 5802 and second 5804 markers are visible under imaging.

All components of the catheter assemblies, catheters, an introducers can be made from any suitable material. Non-limiting examples of materials considered suitable for use in inventive devices include known, conventional, and later-developed materials considered suitable for use in the making of catheter assemblies, catheters, and introducers. Non-limiting examples of materials currently considered suitable by the inventors include polymeric, metal, and alloy materials conventionally used in the making of catheter assemblies, catheters, and introducers.

The catheters and catheter assemblies described and illustrated herein are examples selected from various catheters and catheter assemblies that lie within the scope of the invention. The described and illustrated examples were selected, in part, to demonstrate various structures and characteristics within the scope of the invention. As such, it should be noted that the structures and characteristics of one example embodiment can be combined with one or more structures and characteristics of another example embodiment in a manner consistent with the invention.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

We claim:

1. A catheter for extracorporeal circulation of body fluids, comprising:
    an elongate member having a proximal end defining an infusion port and a drainage port, a distal end defining a distal opening, a proximal portion extending from the proximal end toward the distal end, a distal portion extending from the distal end toward the proximal end along a first longitudinal axis, a main body extending between the proximal and the distal portion along a second longitudinal axis substantially parallel to the first longitudinal axis, an offset portion extending between the main body and the distal portion, and a circumferential wall extending between the proximal and distal ends;
    the main body having a first outer diameter that is substantially uniform along the axial length of the main body;
    the circumferential wall having an internal surface defining an internal lumen, defining an infusion opening, and defining a first set of drainage openings on the main body and a second set of drainage openings on the distal portion, the infusion opening and each drainage opening of the first and second sets of drainage openings comprising a passageway through the thickness of the circumferential wall;
    a septum disposed on and continuous with the internal surface of the circumferential wall, the septum dividing the internal lumen into fluidicly isolated drainage and infusion lumens;
    the drainage lumen extending between the drainage port and the distal opening, each opening of the first and second sets of drainage openings providing fluid access to the drainage lumen; and
    the infusion lumen extending between the infusion port and the infusion opening, wherein the infusion opening is disposed on the distal portion, axially between the first and second sets of drainage openings.

2. The catheter of claim 1, wherein the infusion opening is disposed on the distal portion, axially distal to the first and second sets of drainage openings and proximal to the distal opening.

3. The catheter of claim 2, wherein the first set of drainage openings extends along only a portion of the circumference of the main body.

4. The catheter of claim 3, wherein the second set of drainage openings extends along only a portion of the circumference of the distal portion.

5. The catheter of claim 4, wherein each of the first and second sets of drainage openings is disposed substantially on a first axial side of the elongate member and the infusion opening is disposed substantially on a second, substantially opposite axial side of the elongate member.

6. The catheter of claim 1, wherein the first set of drainage openings extends along only a portion of the circumference of the main body.

7. The catheter of claim 6, wherein the second set of drainage openings extends along the entire circumference of the distal portion.

8. The catheter of claim 7, wherein the first set of drainage openings is disposed substantially on a first axial side of the elongate member and the infusion opening is disposed substantially on a second, substantially opposite axial side of the elongate member.

9. A catheter for extracorporeal circulation of body fluids, comprising:
    an elongate member having a proximal end defining an infusion port and a drainage port, a distal end defining a distal opening, a proximal portion extending from the proximal end toward the distal end, a distal portion extending from the distal end toward the proximal end along a first longitudinal axis, a main body extending between the proximal and the distal portion along a second longitudinal axis substantially parallel to the first longitudinal axis, an offset portion extending between the main body and the distal portion, and a circumferential wall extending between the proximal and distal ends;
    the main body having a first outer diameter that is substantially uniform along the axial length of the main body;
    the circumferential wall having an internal surface defining an internal lumen, defining an infusion opening, and defining a first set of drainage openings on the main body and a second set of drainage openings on the distal portion, the infusion opening and each drainage opening of the first and second sets of drainage openings comprising a passageway through the thickness of the circumferential wall;
    the first set of drainage openings disposed substantially on a first axial side of the elongate member and extending along only a portion of the circumference of the main body;
    the infusion opening disposed substantially on a second, substantially opposite axial side of the elongate member;
    the second set of drainage openings extending along the entire circumference of the distal portion;
    a septum disposed on and continuous with the internal surface of the circumferential wall, the septum dividing the internal lumen into fluidicly isolated drainage and infusion lumens;
    the drainage lumen extending between the drainage port and the distal opening, each opening of the first and second sets of drainage openings providing fluid access to the drainage lumen; and the infusion lumen extending between the infusion port and the infusion opening, wherein the infusion opening is disposed on the distal portion, axially between the first and second sets of drainage openings.

10. The catheter of claim 9, wherein the infusion opening is disposed on the distal portion, axially distal to the first and second sets of drainage openings and proximal to the distal opening.

11. The catheter of claim 9, further comprising a series of radiographic markers embedded in the circumferential wall in the main body, proximal to and adjacent the infusion opening.

12. The catheter of claim 11, wherein the series of radiographic markers comprises an odd number of radiographic markers, with a first subset of radiographic markers of the series of radiographic markers comprising an even number of radiographic markers disposed on a first axial side of the infusion opening and a second subset of radiographic markers of the series of radiographic markers comprising an odd number of radiographic markers disposed on the second, opposite axial side of the infusion opening.

13. The catheter of claim 12, wherein the series of radiographic markers comprises three radiographic markers, the first subset of radiographic markers of the series of radiographic markers comprises two radiographic markers, and the second subset of radiographic markers of the series of radiographic markers comprises one radiographic marker.

14. The catheter of claim 9, further comprising a reinforcement mesh embedded in the circumferential wall in the main body, the reinforcement mesh having a mesh proximal end and a mesh distal end;

a first annular ring embedded within the circumferential wall radially outward of the mesh proximal end; and a second annular ring embedded within the circumferential wall radially outward of the mesh distal end;

wherein the first annular ring forms a first annular bump in the circumferential wall above the mesh proximal end and the second annular ring forms a second annular bump in the circumferential wall above the mesh distal end.

15. The catheter of claim 14, wherein the reinforcement mesh comprises a series of parallel circumferential members joined with a series of parallel axial members forming a plurality of regularly spaced and sized openings.

16. The catheter of claim 15, wherein the reinforcement mesh comprises a partial ring structure having a longitudinal slit extending from the mesh proximal end to the mesh distal end.

17. The catheter of claim 14, wherein the reinforcement mesh is disposed axially proximal to the infusion opening and the first and second sets of drainage openings.

18. A catheter for extracorporeal circulation of body fluids, comprising:

an elongate member having a proximal end defining an infusion port and a drainage port, a distal end defining a distal opening, a proximal portion extending from the proximal end toward the distal end, a distal portion extending from the distal end toward the proximal end along a first longitudinal axis, a main body extending between the proximal and the distal portion along a second longitudinal axis substantially parallel to the first longitudinal axis, an offset portion extending between the main body and the distal portion, and a circumferential wall extending between the proximal and distal ends;

the main body having a first outer diameter that is substantially uniform along the axial length of the main body;

the circumferential wall having an internal surface defining an internal lumen, defining an infusion opening, and defining a first set of drainage openings on the main body and a second set of drainage openings on the distal portion, the infusion opening and each drainage opening of the first and second sets of drainage openings comprising a passageway through the thickness of the circumferential wall;

the first set of drainage openings disposed on a first side of the elongate member and extending along only a portion of the circumference of the main body;

the infusion opening disposed on the distal portion, axially between the first and second sets of drainage openings, on a second side of the elongate member;

the second set of drainage openings extending along the entire circumference of the distal portion;

a series of radiographic markers embedded in the circumferential wall in the main body and arranged in an asymmetrical pattern relative to the infusion opening;

a reinforcement mesh embedded in the circumferential wall in the main body, the reinforcement mesh having a mesh proximal end and a mesh distal end;

a first annular ring embedded within the circumferential wall radially outward of the mesh proximal end;

a second annular ring embedded within the circumferential wall radially outward of the mesh distal end;

a septum disposed on and continuous with the internal surface of the circumferential wall, the septum dividing the internal lumen into fluidically isolated drainage and infusion lumens;

the drainage lumen extending between the drainage port and the distal opening, each opening of the first and second sets of drainage openings providing fluid access to the drainage lumen; and the infusion lumen extending between the infusion port and the infusion opening.

* * * * *